United States Patent [19]

Owen et al.

[11] Patent Number: 4,633,028

[45] Date of Patent: Dec. 30, 1986

[54] PROCESS FOR CONVERTING OXYGENATES TO ALKYLATED LIQUID HYDROCARBONS

[75] Inventors: Hartley Owen, Belle Mead; Samuel A. Tabak, Wenonah; Bernard S. Wright, East Windsor, all of N.J.

[73] Assignee: Mobil Oil Corporation, New York, N.Y.

[21] Appl. No.: 779,367

[22] Filed: Sep. 23, 1985

[51] Int. Cl.$^4$ .............. C07C 1/20; C07C 2/00
[52] U.S. Cl. .................. 585/331; 585/315; 585/316; 585/640; 585/709; 585/723
[58] Field of Search ............. 585/331, 315, 316, 640, 585/709, 723

[56] References Cited

U.S. PATENT DOCUMENTS

| | | | |
|---|---|---|---|
| 3,972,958 | 8/1976 | Garwood et al. | 585/469 |
| 4,048,250 | 9/1977 | Garwood et al. | 585/469 |
| 4,211,885 | 7/1980 | Banks | 585/415 |
| 4,262,155 | 4/1981 | Hutson, Jr. | 585/331 |
| 4,423,274 | 12/1983 | Daviduk et al. | 585/640 |
| 4,482,772 | 11/1984 | Tabak | 585/254 |
| 4,506,106 | 3/1985 | Hsia et al. | 585/312 |
| 4,543,435 | 9/1985 | Gould et al. | 585/330 |
| 4,547,602 | 10/1985 | Tabak | 585/314 |

Primary Examiner—Asok Pal
Attorney, Agent, or Firm—A. J. McKillop; M. G. Gilman; L. G. Wise

[57] ABSTRACT

Alkylate is produced by catalytically converting oxygenate feedstock, such as methanol, to lower olefins comprising $C_2$–$C_4$ olefins. Ethene is separated by interstage sorption of $C_3+$ components and an isoparaffin is alkylated with $C_3$–$C_4$ olefins derived from sorbate.

The improved technique comprises fractionating an olefinic feedstream containing ethene and $C_3+$ olefinic components by contacting the olefinic feedstream in a sorption zone with a liquid hydrocarbon sorbent to selectively sorb $C_3+$ components; reacting $C_3+$ olefins with excess isoparaffin in a catalytic alkylation reactor to produce $C_7+$ alkylate hydrocarbons; fractionating the alkylation reactor effluent to provide a liquid hydrocarbon fraction rich in $C_7+$, alkylate for recycle to the sorption zone as lean sorbent; and recovering $C_7+$ alkylate product and $C_5+$ gasoline from the process.

16 Claims, 3 Drawing Figures

PROCESS FOR CONVERTING OXYGENATES TO ALKYLATED LIQUID HYDROCARBONS

BACKGROUND OF THE INVENTION

This invention relates to an integrated system for converting oxygenates, such as methanol or dimethyl ether (DME), to liquid hydrocarbons. In particular it provides a continuous process for producing $C_7^{30}$ hydrocarbon products by converting the oxygenate feedstock catalytically to an intermediate lower olefinic stream and alkylating isobutane or other isoparaffins with olefins to produce light distillate and/or gasoline products.

In order to provide an adequate supply of liquid hydrocarbons for use as synfuels or chemical feedstocks, various processes have been developed for converting coal and natural gas to gasoline and distillate. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for making diesel fuel by a multi-stage technique.

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of new industrial processes.

The medium pore ZSM-5 type catalysts are useful for converting methanol and other lower aliphatic alcohols or corresponding ethers to olefins. Particular interest has been directed to a catalytic process for converting low cost methanol to valuable hydrocarbons rich in ethene and $C_3+$ alkenes. Various processes are described in U.S. Pat. Nos. 3,894,107 (Butter et al), 3,928,483 (Chang et al), 4,025,571 (Lago), 4,423,274 (Daviduk et al), 4,433,189 (Young), and 4,543,435 (Gould and Tabak), incorporated herein by reference. It is generally known that the MTO process can be optimized to produce a major fraction of $C_2$-$C_4$ olefins. Prior process proposals have included a separation section to recover ethene and other gases from byproduct water and $C_5+$ hydrocarbon liquids.

SUMMARY OF THE INVENTION

It has been discovered that methanol, DME or the like may be converted to liquid fuels, particularly alkylate, in a multi-stage continuous process, with integration between the major process units providing an ethene-rich recycle stream for further conversion and an alkylate recycle stream for interstage sorption. The initial stage MTO type process hydrocarbon effluent stream, after byproduct water separation, can be fed to an alkylation stage for conversion to heavier hydrocarbons. Ethene may be recovered by interstage separation and recycled. Advantageously, the recycled ethene is found to be reactive with methanol/DME or other oxygenates in the presence of ZSM-5 type catalysts. In effect a novel MTO-Alkylation system is provided wherein the ethene component may be recycled sustantially to extinction.

In a preferred embodiment, the invention provides processes and apparatus for an integrated continuous technique for converting oxygenated organic feedstock to liquid alkylate hydrocarbons comprising methods and means for (a) contacting feedstock with zeolite catalyst in a primary catalyst stage at elevated temperature to convert at least a portion of the feedstock oxygenate predominantly $C_2$-$C_4$ olefins and a minor fraction containing $C_5+$ hydrocarbons;

(b) cooling and separating effluent from step (a) to provide an aqueous liquid byproduct stream, a heavy hydrocarbon liquid stream and a light hydrocarbon vapor stream rich in $C_2$-$C_4$ olefins;

(c) compressing at least a portion of the olefinic light hydrocarbon stream to condense a liquid olefinic hydrocarbon stream rich in $C_3$-$C_4$ olefins and recovering an ethene-rich gaseous stream;

(d) contacting the light hydrocarbon vapor stream from step (c) with a liquid hydrocarbon sorbent stream in a sorption tower under conditions to selectively sorb the major amount of $C_3+$ hydrocarbon components from said light vapor stream to provide a sorbate stream rich in $C_3$-$C_4$ olefins.

(e) further reacting the condensed liquid olefinic hydrocarbon stream from step (c) and the sorbate stream from step (d) with isoparaffin in a secondary alkylation stage with liquid phase acid catalyst to convert at least a portion of $C_3$-$C_4$ olefins to a heavier $C_7+$ liquid hydrocarbon product stream comprising alkylate gasoline;

(f) recycling ethene in a gaseous stream to the primary catalytic stage; and (g) recycling a portion of alkylate gasoline to step (d) for use as lean sorbent.

Advantageously, the primary stage catalyst comprises ZSM-5 type zeolite and ethene is recycled to the primary stage at a rate of about 1 to 20 parts ethene per 100 parts by weight of methanol equivalent in the feedstock. By fractionating gaseous effluent separated from the primary staged effluent, a recycle gas stream may be recovered containing at least 90% of ethene from the primary catalytic stage. An olefinic stream rich in $C_3+$ olefins, especially propene and butylenes, is provided for reaction with various isoparaffins, such as isobutane.

Other objects and features of the invention will be seen in the following description and drawings.

THE DRAWINGS

DESCRIPTION OF PREFERRED EMBODIMENTS

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($CH_3OH + CH_3OCH_3 + H_2O$) is produced by partial dehydration. This reaction takes place in either conversion of methanol to lower olefins (MTO) or methanol to gasoline (MTG).

The zeolite catalysts preferred for use herein include the crystalline aluminosilicate zeolites having a silica to alumina ratio of at least 12, a constraint index of about 1 to 12 and acid cracking activity of about 1–200. Representative of the ZSM-5 type zeolites are ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for oxygenate conversion is HZSM-5 zeolite with alumina binder. These medium pore shape selective catalysts are sometimes known as porotectosilicates or "pentasil" catalysts.

Other catalysts and processes suitable for converting methanol/DME to lower olefins are disclosed in U.S. Pat. No. 4,393,265 (Bonifaz), U.S. Pat. No. 4,387,263 (Vogt et al.) and European Patent Application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and ethylene conversion.

In this description, metric units and parts by weight are employed unless otherwise stated. Various reactor configurations may be used, including fluidized bed catalytic reactors, moving bed and fixed bed reactors.

Figure 1:
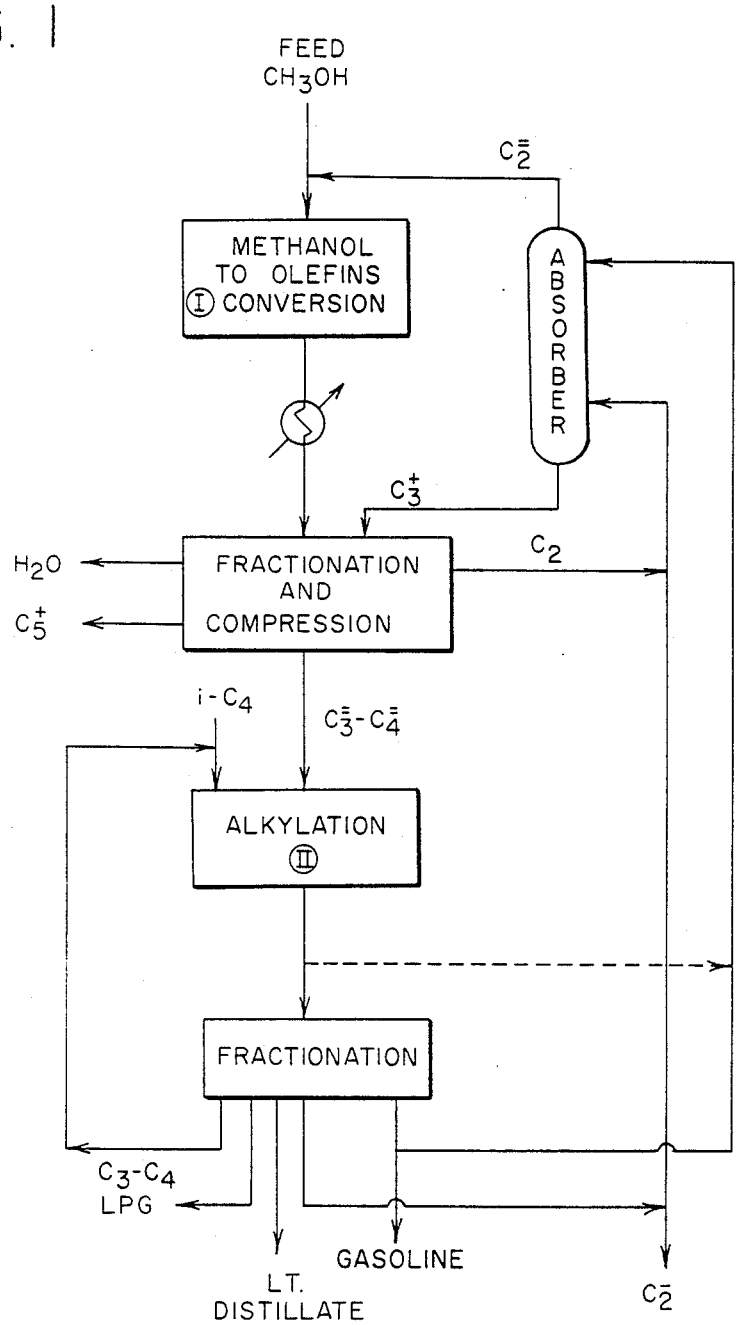
FIG. 1 is a process flow sheet showing the major unit operations and process streams.

Referring to FIG. 1, the process feedstock (methanol or DME, for instance) is fed to the primary MTO stage (I) where it is converted to lower olefins and $C_5+$ gasoline hydrocarbon plus water by dehydration of the oxygenated feedstock. Byproduct water is recovered by simple phase separation from the cooled effluent. Liquid hydrocarbons consisting essentially of $C_5+$ gasoline range materials may be recovered or pumped to the higher secondary stage pressure. Vapor phase effluent from the primary stage may be compressed to alkylation reaction pressure. Propylene, butylenes and amylenes may be separated from the primary stage effluent by sorption fractionation to recover a recycle gas stream containing at least 90% of ethene from the primary stage and an olefinic sorbate stream rich in $C_3+$ olefins. A $C_3-C_4$ rich olefinic stream may be further prepared for reaction with isobutane or the like at high pressure and low temperature in contact with liquid phase acidic alkylation catalyst. Secondary stage (II) alkylation effluent is then separated into $C_2$-light gases, $C_3-C_4$ aliphatics and $C_5+$ gasoline and/or light distillate range hydrocarbons. Advantageously, isobutane is separated from the second stage effluent for recycle to provide a stoichiometric excess and added with fresh feed ($i-C_4$) to the unit. A portion of the liquid alkylate-rich hydrocarbon is recycled to the interstage sorption unit as lean sorbent. The preferred sorption unit is a countercurrent packed tower. Advantageously, the sorbent liquid comprises at least 75 wt% of $C_7$ to $C_9$ isoparaffins which are the alkylate reaction product. This lean sorbent has excellent properties for selective sorption of the propene, butylene and $C_3+$ paraffinic components of the primary stage light hydrocarbons. Unfractionated liquid alkylation effluent may be recycled in part, as depicted by dashed line.

The process may be optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock. Suitable equipment and operating conditions are described in U.S. patent application Ser. No. 687,045, filed Dec. 28, 1984, incorporated herein by reference.

Figure 2:
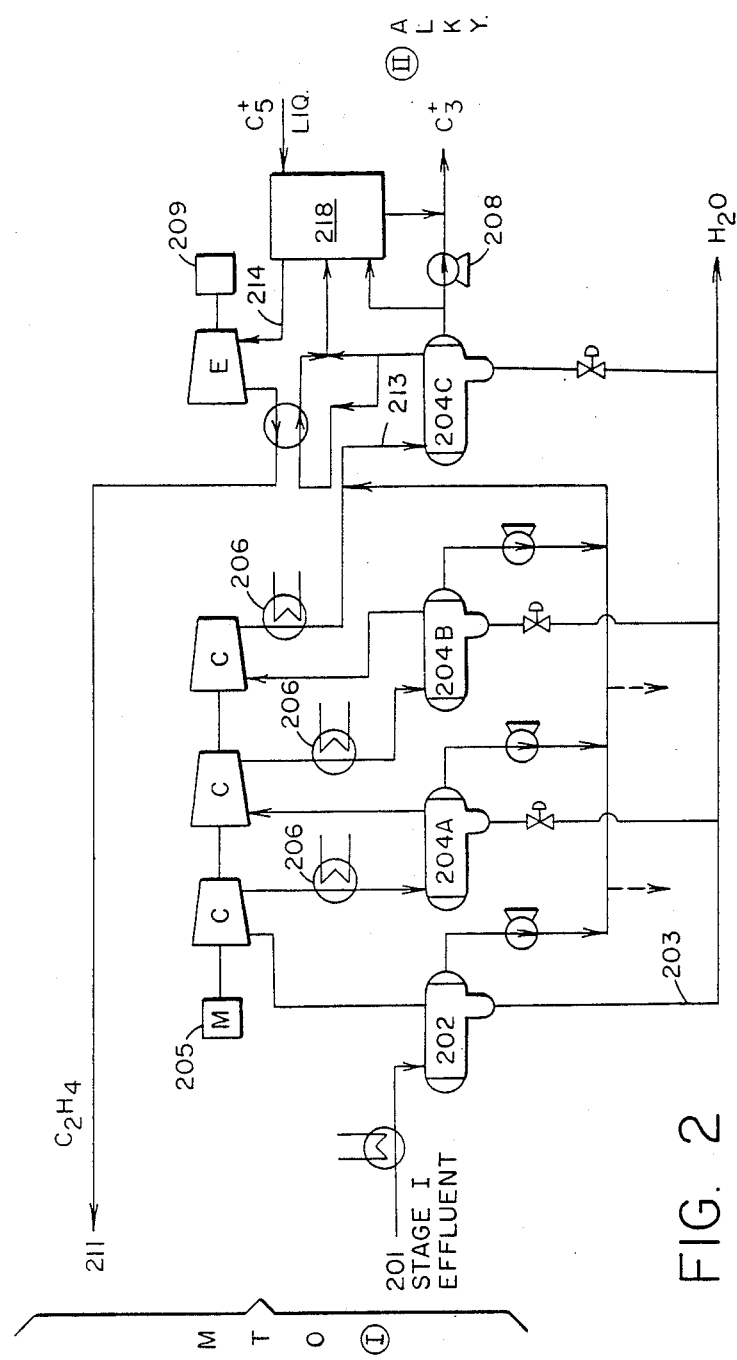
FIG. 2 is a schematic representation of a preferred inter-stage separation system for ethene recovery.

In the embodiment of FIG. 2, the light hydrocarbon vapor stream separated from the primary stage effluent is compressed in a plurality of compression stages to condense liquid olefinic hydrocarbons. The full reaction effluent of the primary stage MTO plant is passed via conduit 201 and primary phase separator 202 to provide a first vapor stream rich in $C_4$-hydrocarbons, liquid hydrocarbons stream, and byproduct water stream. The liquid (eq-$C_5+$) stream is combined with a corresponding liquid HC from succeeding separators and withdrawn. The primary vapor stream is adiabatically compressed by multi-stage compressor 205, cooled via exchanger 206 and passed to a succeeding separator 204A, at which point the preceeding phase separation technique is repeated. Likewise other separators 204B and 204C operate to provide an ethene-rich recycle stream which is passed via line 214 to turboexpander 209 and thus at MTO pressure back via line 211 to the olefins production in the primary stage. Advantageously, the MTO effluent is received at about atmospheric pressure (eg, $100 \propto 150$ kPa) and compressed in plural stages to a pressure of about 1100–3500 kPa (150–400 psig) and separated in the final vessel 204C at about ambient temperature (20°–80° C.). Olefinic liquids rich in $C_3+$ aliphatic are recovered from the final compressor stage via pump 208 which passes the liquid hydrocarbon stream to the following secondary stage alkylation unit.

Ethene-rich vapor withdrawn from the separator 204C via line 213 is cooled by heat exchange and further processed to increase ethene purity in sorption unit 216. A suitable selective sorption unit is disclosed in U.S. Pat. No. 4,497,968 (Hsia et al), incorporated herein by reference. Preferably, compressed light hydrocarbons are fractionated by sorption to recover a recycle stream containing at least 90 mole percent ethene. This can be achieved by selectively absorbing $C_3+$ components in a $C_5+$ liquid hydrocarbon sorbent stream, especially $C_7$ to $C_9$ alkylate.

Figure 3:
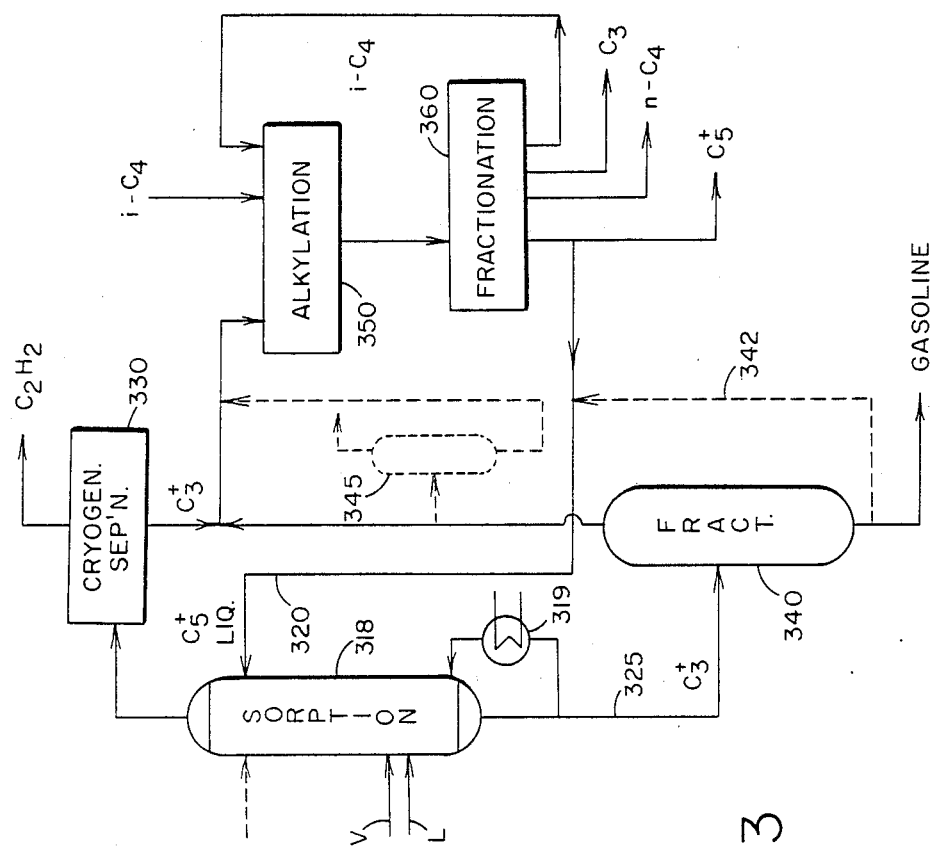
FIG. 3 is an alternative process flow sheet depicting sorption, fractionation and alkylation units schematically.

Interstage fractionation can be modified within the inventive concept to provide for recovery of purified ethylene ($C_2H_2$) and heavier hydrocarbon liquids. In FIG. 3, a sorption fractionator unit 318, comprising a vertical countercurrent contact tower, is equipped with a bottom reboiler means 319. Sorbent liquid, rich in $C_7$ to $C_9$ alkylate, is introduced via conduit 320. Optionally, other $C_5+$ liquids may be employed to supplement the alkylate stream. A light olefin feedstream containing $C_2-C_4$ alkenes is introduced via vapor conduit V and liquid conduit L. The sorber overhead may contain 40% or more ethene, which can be further purified by cryogenic separation unit 330 to remove any remaining $C_3+$ hydrocarbons and thus to recover pure ethene.

The sorbate stream 325, rich in $C_3$-$C_4$ alkenes, is fractionated in distillation tower 340 to recover gasoline range hydrocarbons, this tower may be operated to obtain a heavy $C_6$ product, with $C_5$ components passing either overhead or with the bottoms. Optionally, this overhead fraction is de-ethanized by tower 345, and the liquified sorbate fraction, rich in $C_3$-$C_4$ components is combined with $C_3+$ components from the cryogenic separation unit and fed at high pressure (e.g., up to 3000 kPa) to alkylation reactor unit 350, where it is contacted with an isoparaffin, such as isobutane (i-$C_4$) in the presence of an alkylation catalyst to produce alkylate hydrocarbons. The alkylation fractionation system 360 may be operated in a known manner to separate the reactor effluent into several fractions, including i-$C_4$ recycle to provide excess isoparaffin, light gas ($C_3$), normal paraffin (n-$C_4$) and $C_5+$ liquid. At least a portion of the $C_5+$ components, especially the $C_7$ to $C_9$ alkylate reaction products, is passed via conduit 320 to the sorption fractionator unit as lean sorbent. Recovered $C_5+$ liquids from fractionation unit 360 may be further refined to recover aviation gasoline, light distillate, etc. If additional sorbent liquid is required, a bottom fraction from unit 340 may be utilized, as indicated by dashed line 342. However, it is preferred to employ sorbent comprising a major amount of $C_7$-$C_9$ hydrocarbons, particularly at least 75% paraffinic alkylate.

The data in Table I represents a material balance and absorber operating conditions for a countercurrent contact tower unit design according to FIG. 3 and Runs 1-3. The vertical tower has 21 theoretical stages, with $C_7$-$C_9$ alkylate (lean oil #1) from second stage product fractionator being introduced at the top (stage 1), heavy liquid separated from the MTO effluent (lean oil #2) being introduced at stage 5, olefin vapor and liquid feed being fed at stages 12 and 13 respectively. Heat of sorption is removed by pumparound cooling at stages 5 and 8. The three runs correspond to different lean oil rates. In the overhead stream, molar units are gm-moles per metric tonne (MT) of methanol (MeOH) charged to the process. The operating conditions are chosen to provide a maximum ethene content of 0.2 mol % in the sorbate.

TABLE 1

| ABSORBER OPERATION* | | | |
|---|---|---|---|
| Run No. | 1 | 2 | 3 |
| Material Balance wt % of MeOH charge | | | |
| (1) $C_6+$ MTO Gasoline | 50.0 | 22.0 | 17.6 |
| (2) Alkylate | 15.3 | 47.3 | 51.7 |
| (3) n-butane | 4.9 | 1.0 | 0.8 |
| (4) propane | 3.9 | 3.8 | 3.8 |
| (5) offgas | 1.5 | 1.5 | 1.6 |
| (6) water | 56.4 | 56.4 | 56.4 |
| (7) i-$C_4$ makeup | −32.0 | −32.0 | −31.9 |
| (8) methanol | −100.0 | −100.0 | −100.0 |
| Absorber* | | | |
| Lean Oil #1 (stage 1) g-moles/tonne MeOH | 4.44 | 1.19 | 0.69 |
| Lean Oil #2 (stage 5) g-moles/tonne MeOH | 1.01 | 1.01 | 1.01 |
| TOTAL | 5.45 | 2.20 | 1.70 |
| overhead flow, SCM/ton MeOH | 42.0 | 45.3 | 49.5 |
| propane, g-moles/tonne MeOH | 0.0 | 6.5 | 18.5 |
| propylene | 1.0 | 120.4 | 280.0 |
| n-butane | 3.9 | 18.3 | 18.1 |
| isobutane | 0.1 | 0.6 | 1.5 |
| 1-butylene | 0.0 | 1.0 | 5.4 |
| n-pentanes | 0.7 | 0.6 | 0.6 |
| iso-pentanes | 40.2 | 30.0 | 28.4 |
| pentanes | 0.0 | 0.0 | 0.1 |
| $C_6+$ | 16.5 | 17.4 | 17.9 |
| Overhead pressure, kPa | 2068 | 2068 | 2068 |
| Cooling pump around, MJ/ tonne MeOH | −36.7 | −35.4 | −31.7 |
| Reboiler Duty, MS/tonne MeOH | 206.1 | 106.6 | 94.2 |
| Ethylene recovery in overhead g-moles/ tonne MeOH | 938 | 938 | 938 |
| Mole % purity | 53 | 49 | 45 |

*based on 0.2 mol % $C_2$ in bottoms

Runs 4 to 6 (Table II) are similar to Runs 1 to 3, except that the paraffinic lean oil is alkylation reactor effluent containing 78 mole % isobutane, 6% $C_7$-$C_9$ alkylate and $C_5-$ hydrocarbons.

TABLE II

| ABSORBER OPERATION | | | |
|---|---|---|---|
| Run No. | 4 | 5 | 6 |
| Material Balance wt % of MeOH charge | | | |
| (1) $C_6+$ MTO gasoline | 15.0 | 12.3 | 11.9 |
| (2) Alkylate | 53.6 | 57.2 | 57.5 |
| (3) n-butane | 0.8 | 0.7 | 0.7 |
| (4) propane | 4.8 | 4.0 | 3.9 |
| (5) offgas | 1.5 | 1.5 | 1.6 |
| (6) water | 56.4 | 56.4 | 56.4 |
| (7) i$C_4$ | −32.1 | −32.1 | −32.0 |
| (8) methanol | −100.0 | −100.0 | −100.0 |
| Absorber Efficiency* | | | |
| Lean Oil #1 (stage 5) g-moles/tonne·Meort | 4.44 | 1.09 | 0.54 |
| Lean Oil #2 (stage 1) g-moles/ton MeOH | 1.01 | 1.01 | 1.01 |
| Total | 5.45 | 2.10 | 1.55 |
| Overhead flow, SCM/ton MeOH | 45.8 | 46.7 | 50.3 |
| propene, g-moles/ tonne MeOH | 47.7 | 37.2 | 36.4 |
| propylene | 36.1 | 97.2 | 252.1 |
| n-butane | 3.3 | 2.7 | 2.5 |
| isobutane | 62.7 | 47.7 | 39.7 |
| i-butylene | 34.9 | 35.7 | 36.5 |
| n-pentanes | 0.6 | 0.6 | 0.6 |
| iso-pentanes | 4.9 | 5.0 | 5.0 |
| pentenes | 13.0 | 13.3 | 13.5 |
| $C_6+$ | 12.8 | 13.1 | 13.1 |
| Overhead pressure, kPa | 2068 | 2068 | 2068 |
| Cooling Pump around, MJ/tonne MeOH | −37.7 | −27.9 | −21.0 |
| Reboiler Duty, MJ/ tonne MeOH | 152.2 | 95.2 | 85.6 |
| Ethylene recovery in overhead g-moles/tonne MeOH | 939 | 939 | 939 |
| Mole % purity | 49 | 48 | 44 |

*based on 0.2 mol % $C_2$ in bottoms

The alkylation process employed herein is a well known industrial technique for reacting alkenes with tertiary alkanes (isoparaffins), such as isobutane, isopentane, isohexane, etc. The resulting product is a $C_7+$ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21-41 MPa (3000-6000 psi). Under these conditions, both normal and isoparaffins can be brought into reaction by a free-radical mechanism. Thermal alkylation is not known to be practiced commercially.

The catalytic alkylation of paraffins involves the addition of an isoparaffin containing a tertiary hydrogen to an olefin. The process is used in the petroleum industry to prepare highly branched paraffins mainly in the $C_7$ to $C_9$ range, that are high-quality fuels. The overall process is complex, requiring control of operating conditions and of catalyst. The process conditions and the product composition depend on the particular hydrocarbons involved.

The preferred processes are those brought about by the conventional protonic and Lewis catalysts. Propene can be brought into reaction with an isoparaffin in the presence of either concentrated sulfuric acid or hydrogen fluoride. The heptanes produced by alkylation of isobutane with propene are mainly 2,3- and 2,4-dimethyloentane. Propene is alkylated preferrably as a component of a $C_3$-$C_4$ fraction. HF catalysts for alkylation of isobutane with 1- and 2-butenes give both dimethylhexanes and trimethylpentanes. The product obtained from alkylation of isobutane with isobutylene at low temperature (e.g., $-25°$ C.) with hydrogen fluoride is 2,2,4-trimethylpentane.

During use the acid catalysts may become diluted with byproduct hydrocarbons and as a result decrease in activity. Sulfuric acid concentrations are maintained at about 90%. Hydrogen fluoride concentrations of 80–90% are common, although the optimum concentration depends on the reaction temperature and reactor geometry. Operation below these acid concentrations generally causes incomplete conversion or polymerization. With sulfuric acid, the product quality is improved when temperatures are reduced to the range of $0°$–$10°$ C. Cooling requirements are obtained by low temperature flashing of unreacted isobutane. With hydrogen fluoride, the reaction process is less sensitive to temperature, and temperatures of $0°$–$40°$ C. can be used. Some form of heat removal is essential because the heat of reaction is approximately $14 \times 10^5$ J/kg (600 Btu/lb) of butenes converted. Typically the elevated pressure for alkylation by these acid catalysts is about 1500 to 3000 kPa (200–300 psig).

In order to prevent polymerization of the olefin as charged, an excess of isobutane is present in the reaction zone. Isobutane-to-olefin molar ratios of 6:1 to 14:1 are common, more effective suppression of side reactions being produced by the higher ratios.

The typical alkylation reaction employs a two-phase system with a low solubility of the isobutane in the catalyst phase. In order to ensure intimate contact of reactants and catalyst, efficient mixing is provided. This is important with sulfuric acid because of the low solubility of isobutane in the catalyst phase. In addition, the higher viscosity of the sulfuric acid requires a greater mixing energy to assure good contact. The solubility of the hydrocarbon reactants in the catalyst phase is increased by the presence of the unsaturated organic diluent held by the acid catalyst. This organic diluent also has been considered a source of carbonium ions that promote the alkylation reaction.

For the hydrofluoric acid system, reactive $i$-$C_4H_8$ readily alkylates to give an excellent product. The alkylation of pure 1-$C_4H_8$ by itself proceeds with considerable isomerization of the 1-$C_4H_8$ to 2-$C_4H_8$ followed by alkylation to give a highly branched product. The presence of $i$-$C_4H_8$ accelerates the alkylation reaction and allows less time for olefin isomerization. Consequently the reaction produces an alkylate with a lowered antiknock value. For the sulfuric acid system, $i$-$C_4H_8$ tends to oligomerize and causes other side reaction products of inferior quality; but the isomerization of 1-$C_4H_8$ to 2-$C_4H_8$ proceeds more completely, thereby favoring formation of superior products. Thus for mixed olefin feeds such as described above, the two factors with both catalyst systems counteract each other to provide products of similar antiknock properties.

The olefin-producing MTO process may simultaneously generate isobutane, but the amount may be insufficient to alkylate the coproduced olefins. A suitable outside source of isobutane is natural gas or a byproduct of methanol-to-gasoline (MTG) processes.

Suitable alkylation processes are described in U.S. Pat. Nos. 3,879,489 (Yurchak et al), 4,115,471 (Kesler), 4,377,721 (Chester) and in the Kirk-Othmer Encyclopedia of Chemical Technology, Vol. 2, pp. 50–58 (3rd Ed., 1978) John Wiley & Sons, incorporated herein by reference.

The combined processes are an effective means for converting oxygenated organic compounds, such as methanol, DME, lower aliphatic ketones, aldehydes, esters, etc, to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

We claim:
1. An integrated continuous process for converting oxygenated organic feedstock to liquid hydrocarbons comprising the steps of
   (a) contacting feedstock with zeolite catalyst in a primary catalyst stage at elevated temperature to convert at least a portion of the feedstock oxygenate predominantly to $C_2$-$C_4$ olefins and a minor fraction containing $C_5+$ hydrocarbons;
   (b) cooling and separating effluent from step (a) to provide an aqueous liquid byproduct stream, a heavy hydrocarbon liquid stream and a light hydrocarbon vapor stream rich in $C_2$-$C_4$ olefins;
   (c) compressing at least a portion of the olefinic light hydrocarbon stream to condense a $C_3+$ liquid olefinic hydrocarbon stream rich in $C_3$-$C_4$ olefins and recovering an ethene-rich gaseous stream;
   (d) contacting the light hydrocarbon vapor stream from step (c) with a liquid hydrocarbon sorbent stream in a sorption tower under conditions to selectively sorb the major amount of $C_3+$ hydrocarbon components from said light vapor stream to provide a $C_3+$ sorbate stream rich in $C_3$-$C_4$ olefins.
   (e) fractionating $C_3+$ sorbate to provide $C_5+$ gasoline and a $C_3$-$C_4$ olefin stream;
   (f) further reacting the $C_3$-$C_4$ olefin stream from step (e) with isoparaffin in a secondary alkylation stage with liquid phase acid catalyst to convert at least a portion of $C_3$-$C_4$ olefins to a heavier $C_7+$ liquid hydrocarbon product stream comprising alkylate gasoline;
   (g) recycling ethene for further catalytic conversion in the primary catalytic stage; and

(h) recycling a portion of alkylate gasoline to step (d) for use as lean sorbent.

2. The process of claim 1 further comprising the step of fractionating gaseous effluent from separation step (b) to recover a recycle gas stream containing at least 90% of ethene from the primary catalytic stage and an olefinic stream rich in $C_3+$ olefins.

3. The process of claim 1 wherein the primary stage catalyst comprises ZSM-5 type zeolite and ethene is recycled to the primary stage at a rate of about 1 to 20 parts ethene per 100 parts by weight of methanol equivalent in the feedstock.

4. The process of claim 1 wherein primary stage feedstock comprising methanol and/or dimethyl ether and recycled ethene are converted over HZSM-5 catalyst to provide a light olefinic hydrocarbon vapor stream comprising a major amount of $C_3$-$C_4$ olefins and a minor amount of ethene.

5. The process of claim 4 wherein olefin production is optimized by employing fluid bed primary stage conditions in the temperature range of about 425° C. to 550° C., a pressure range of about 100° to 800° kPa and weight hourly space velocity range of about 0.5° to 3.0° based on ZSM-5 equivalent catalyst and methanol equivalent in the primary stage feedstock.

6. The process of claim 4 wherein primary stage hydrocarbon effluent contains about 1 to 10 wt. % ethene and about 10 to 60 wt. % $C_3$-$C_4$ olefins.

7. The process of claim 4 wherein ethene is recovered from the primary stage effluent vapor stream by fractionation.

8. The process of claim 1 wherein the alkylation stage effluent is fractionated to provide a liquid hydrocarbon stream comprising $C_7$ to $C_9$ isoparaffins and wherein a portion of said $C_7$ to $C_9$ isoparaffinic fraction is recycled as sorbent liquid.

9. The process of claim 1 wherein the secondary alkylation stage comprises a liquid phase reaction catalyzed by HF.

10. In the process for producing alkylate hydrocarbons by catalytic reaction of isoparaffin with lower olefin, the improvement which comprises:
fractionating an olefinic feedstream containing ethene and $C_3+$ olefinic components by contacting the olefinic feedstream in a sorption zone with a liquid hydrocarbon sorbent to selectively sorb $C_3+$ components;
reacting $C_3+$ olefins with excess isoparaffin in a catalytic alkylation reactor to produce $C_7+$ alkylate hydrocarbons;
fractionating the alkylation reactor effluent to provide a liquid hydrocarbon fraction rich in $C_7+$, alkylate;
introducing said $C_7+$ liquid hydrocarbon fraction to the sorption zone as lean sorbent; and
recovering $C_7+$ alkylate product from the process.

11. The process of claim 10 wherein the alkylation reactor effluent is fractionated to provide an isoparaffin recycle stream for further conversion in the alkylation reactor.

12. The process of claim 1 wherein the alkylation catalyst comprises hydrofluoric acid and the reactor is operated at pressure of about 1500 to 3000 kPa to provide a liquid reaction phase.

13. The process of claim 12 wherein the isoparaffin consists essentially of isobutane and the sorbent contains at least 75 weight percent of $C_7$ to $C_9$ paraffinic hydrocarbons.

14. The process of claim 10 wherein the olefinic feedstream is produced by catalytic conversion of methanol over ZSM-5 catalyst at elevated pressure and wherein ethene is recovered from the sorption zone and said recovered ethene is contacted with the catalyst for further conversion with methanol.

15. The process of claim 14 wherein the alkylation catalyst comprises hydrofluoric acid and the reactor is operated at pressure of about 1500 to 3000 kPa to provide a liquid reaction phase.

16. The process of claim 15 wherein the isoparaffin consists essentially of isobutane and the sorbent contains at least 75 weight percent of $C_7$ to $C_9$ paraffinic hydrocarbons.

* * * * *